United States Patent [19]

Christensen

[11] Patent Number: 4,980,191

[45] Date of Patent: Dec. 25, 1990

[54] METHOD OF MAKING DIGESTIVELY HYDROLYZABLE LOW CALORIE EDIBLE OIL SUBSTITUTES

[75] Inventor: Stephen B. Christensen, Midland, Mich.

[73] Assignee: The Dow Chemical Company, Midland, Mich.

[21] Appl. No.: 444,501

[22] Filed: Nov. 30, 1989

[51] Int. Cl.$^5$ ............................................. A23D 9/00
[52] U.S. Cl. .................................. 426/601; 426/606; 426/607; 426/611
[58] Field of Search ................ 426/601, 606, 607, 611

[56] References Cited

U.S. PATENT DOCUMENTS

| | | | |
|---|---|---|---|
| 2,955,121 | 10/1960 | Myers et al. | 260/407 |
| 3,157,681 | 11/1964 | Fischer | 260/407 |
| 3,412,039 | 11/1968 | Miller | 260/407 |
| 3,422,124 | 1/1969 | Milks et al. | 260/407 |
| 3,732,263 | 5/1973 | Berman | 260/407 |
| 4,005,195 | 1/1977 | Jandacek | 426/658 |
| 4,734,287 | 3/1988 | Singer et al. | 426/602 |
| 4,849,242 | 7/1989 | Kershner | 426/601 |

FOREIGN PATENT DOCUMENTS

| | | |
|---|---|---|
| 0233856 | 8/1987 | European Pat. Off. . |
| 0236288 | 9/1987 | European Pat. Off. . |
| 0303523 | 2/1989 | European Pat. Off. . |

OTHER PUBLICATIONS

Robert G. LaBarge, Food Technology, "The Search for a Low-Caloric Oil," Jan. 1988, pp. 84–90.
A. Jover and R. S. Gordon, Journal of Laboratory Clinical Medicine, "Procedure for Quantitative Analysis of Feces with Special Reference to Fecal Fatty Acids," vol. 59, p. 878 (1962).
F. H. Mattson and G. A. Nolen, Journal of Nutrition, "Absorbability by Rats of Compounds Containing from One to Eight Ester Groups," p. 1171 (1972).
Hamm, Journal of Food Science, "Preparation & Evaluation of Trialkoxytricarballyate, Trialkoxycitrate, Trialkoxyglycerylether, Jojoba Oil & Sucrose Polyester as Low Calorie Replacements of Edible Fats and Oils," 49 (1984) pp. 419–428.

*Primary Examiner*—Donald E. Czaja
*Assistant Examiner*—Helen Pratt

[57] ABSTRACT

Reduced calorie food compositions are produced by replacing at least a portion of the fat content of a conventional food with an improved low calorie edible oil substitute that does not have a laxative effect. This substitute is an esterified form of polymerized $C_{18}$ unsaturated fatty acids that has the property of being at least partly hydrolyzed by the processes of intestinal digestion into simple alcohols and polybasic acids. These polybasic acids are of sufficient molecular weight that they are substantially not absorbed by the intestine, and are thus non-caloric. Since only the alcohol portion contributes calories, the ester as a whole has reduced caloric availability as compared to triglyceride oils. Additionally, the edible oil substitute of this invention has the property of being altered in physical form by said intestinal digestion from an oil of low viscosity into either an oil of high vicosity. This change in physical form is sufficient to avoid the laxative effect common to most low calorie oils.

10 Claims, No Drawings

METHOD OF MAKING DIGESTIVELY HYDROLYZABLE LOW CALORIE EDIBLE OIL SUBSTITUTES

BACKGROUND OF THE INVENTION

The field of this invention is edible compounds and food compositions. More specifically, the invention relates to novel fatty compounds and food compositions based on these compounds. These compounds have the properties of normal triglyceride fats, but are comparatively less absorbed and thus are low in available calories.

In recent years the associated health problems of arteriosclerosis and obesity have raised much concern about the high fat content of the average American diet As a result of these concerns, an increasingly calorie-conscious public has shown great interest in "diet", "lite", and "low calorie" formulations of high calorie fat-based foods. Many of the diet formulations of these foods that are currently available achieve a calorie reduction simply by dilution with water or air. However, by diluting with air or water, there is a reduction of both the perceived quality and "richness" of the food.

A more recent approach is in U.S. Pat. No. 4,734,287 where a suspension of tiny spheres of dairy protein is said to mimic the texture of fat in certain foods such as ice cream or salad dressing. Since this suspension has only about 1.3 calories/g, as compared with 9 calories/g for typical fat, a considerable caloric reduction is possible. Unfortunately, this material cannot be fried or baked and therefore cannot be used as a total fat replacement in all types of snack foods.

A more attractive and versatile approach to this problem is to reduce the fat-related caloric intake by a modification of the fat so as to reduce or prevent the absorption of fat-derived calories. According to Mattson and Nolen, "Absorbability by Rats of Compounds Containing From One to Eight Ester Groups", 102 Journal of Nutrition at 1171 (1972), "the absorbability of a fat is determined by two processes, hydrolysis in the lumen of the intestinal tract and the subsequent absorption of the digestion products". Without this hydrolysis the fat would not be in the form required for intestinal absorption and would simply pass through the body unchanged. If nothing was absorbed, the material would be non-caloric.

The best known example of a material that does not chemically change in the body is Proctor and Gamble's "Olestra" brand of sucrose polyester. Olestra, along with other similar compounds, is reported to have satisfactory organolepitic properties for use in food, but is not absorbed to the same extent as fat due to a low rate of intestinal hydrolysis. Hence, it has a very low caloric availability.

Unfortunately, ingestion of even moderate amounts of this type of material can result in an undesired laxative effect, namely, leakage of the liquid material through the anal sphincter; see D. J. Hamm, "Preparation and Evaluation of Trialkoxytricarballylate, Trialkoxycitrate, Trialkoxyglycerylether, Jojoba Oil and Sucrose Polyester as Low Calories Replacements of Edible Fats and Oils", 49 Journal of Food Science at 419-28 (1984). This anal leakage problem seems to be the inevitable result of the ingestion of an oily material with limited digestibility. To be successful, any fat replacement must be able to avoid this laxative effect. U.S. Pat. No. 4,005,195 teaches another way of avoiding the laxative effect of Olestra by using solid fatty acids and solid fatty acid esters as anti-anal leakage additives to the product. Unfortunately, this solution has the drawback of giving the food composition a "waxy" mouthfeel, due to the high solids content of the mixture.

Additionally, European Patent Application No. 87870021.0, Publication No. 0236288, teaches another way to avoid the laxative effect by preparing a form of Olestra with a non-Newtonian pseudoplastic rheology at body temperature. The special rheology of this material, high viscosity during excretion, but low viscosity during ingestion, is said to prevent anal leakage without adversely affecting the mouthfeel of the product. Yet a second European Patent Application, Publication No. 0233856, teaches that a better tasting low calorie fat material can be formulated by mixing this pseudoplastic form of Olestra with a normal liquid triglyceride. The resulting mixture is said to not taste as "waxy in the mouth" as the special fat substitute alone. However, by mixing a normal liquid triglyceride with the pseudoplastic form of Olestra, it is no longer as low in calories.

What is needed in this area is a low calorie, edible oil substitute that has the physical properties and pleasing mouthfeel of a normal liquid triglyceride oil, but that does not promote a laxative effect.

SUMMARY OF THE INVENTION

This invention is a method for reducing the available calories in a food composition having an edible oil component, which method comprises replacing an effective portion of the edible oil in such food composition with an esterified form of polymerized $C_{18}$ unsaturated fatty acids.

This edible oil replacement, herein to be called "polybasic acid ester", has the property of being at least partly hydrolyzed after ingestion by the processes of intestinal digestion into a mixture comprising polybasic acid and the simple alcohols used to esterify it. The alcohols are absorbed in the normal way and do contribute calories to the mixture. The polybasic acid, however, is of sufficient molecular weight that it is substantially not absorbed by the intestine and is thus non-caloric. Since only the alcohol portion of the ester contributes calories, the ester as a whole has reduced caloric availability as compared to an equal weight of normal triglyceride oil. The amount of polybasic acid ester in the food is an amount sufficient to reduce the caloric availability of the composition. Additionally, it is thought that the polybasic acid ester of this invention has the property of being altered in physical form by said intestinal digestion from an oil of low viscosity into an oil of high viscosity.

In another aspect, this invention is a food composition having an edible oil component with reduced caloric availability in which the edible oil component comprises an amount of said polybasic acid ester effective to reduce the caloric content of the composition.

DETAILED DESCRIPTION OF THE INVENTION

This invention is the use of a polybasic acid ester that is derived from polybasic acids and simple alcohols as a low calorie substitute for oil or fat products that are used in foods. The invention is also a food composition containing the low calorie oil.

This polybasic acid is produced by the terminal polymerization of unsaturated $C_{18}$ fatty acids by a variety of methods that are well known in the art, see for example U.S. Pat. No. 2,955,121: U.S. Pat. No. 3,157,681: U.S. Pat. No. 3,422,124: U.S. Pat. No. 3,412,039 and U.S. Pat. No. 3,732,263: all of which are incorporated by reference herein. If the product of this polymerization is formed by the union of two molecules of fatty acid, the material is commonly known as "dimer acid" and has an approximate molecular weight of 560. If the product of this polymerization is derived by the union of three molecules of fatty acid, the material is commonly known as "trimer acid" and has an approximate molecular weight of 840.

The product from any polymerization process used to produce the polybasic acid typically contains a mixture of unreacted monomeric fatty acids, dimer acids, and trimer acids. The exact ratio of these products depends on the process employed, the feed stock used, and on whether any purification steps are used. Preferably, the polybasic acid used is comprised essentially of a mixture of dimer and trimer acids, with little monomeric fatty acid present. This is because the molecular weights of the dimer and trimer acids are large enough so that the acids are not substantially absorbed in the body by the intestine. Thus, the acids are not absorbed and the dimer and trimer acids are essentially non-caloric. The monomeric fatty acids, however, are absorbed by the intestine, and contribute significantly to the caloric content of the food composition. For this reason the preferred polybasic acid of this invention contains less than about 5 percent and more preferably less than 1 percent of monomeric fatty acid.

The ratio of dimer acid to trimer acid used to polymerize the polybasic acid can be varied according to the desired viscosity of the product ester, and according to the polymerization process used. In general a higher proportion of trimer acid gives a more viscous product. Basically any ratio that is effective as a non-laxative oil replacement can be used. Generally the acid mixture comprises about 1 to about 80 weight percent trimer acid and about 20 to about 99 weight percent dimer acid or any ratios with in these ranges can be used. The preferred mixture is about 40 weight percent dimer and 60 weight percent trimer.

The weight percent of the composition for the preferred mixture will vary depending upon the desired properties of the oil. For example, if one wanted a more viscous low calorie oil then a mixture that contains a higher percentage of the trimer acid would be employed. For most application purposes, it is desirable to have a low calorie oil that has consistency properties which resembles standard oils, such as corn oil, sunflower oil and the like. Suitable feedstocks for this invention include, but are not limited to, tall oil, oleic acid, and linoleic acid. To obtain a viscosity that most closely resembles a standard oil, the ratio of dimer acid to trimer acid in the polybasic acid is from about 80 to about 99 percent dimer acid and from about 20 to about 1 percent trimer acid.

As stated previously, the exact structures of the dimer acids and trimer acids of this invention will vary with the polymerization process used and with the feedstock. In any case the dimer and trimer acids are themselves each comprised of a large number of structural isomers. This large number of isomers is responsible for the fact that these high molecular weight polybasic acids are liquids and not solids. Typical values of the viscosity of the polybasic acid of this invention will vary from, but is not limited to, a value at 100° F. of about 2,000 cPs for a high dimer mixture measured by a Brookfield viscometer, to a value of as much as 22,000 cPs for a high trimer mixture.

The polybasic acid is esterified to form the polybasic ester that is employed as the low calorie oil. The acid is esterified by using a simple alcohol. Generally any means of esterifying the polybasic acid are sufficient to produce the polybasic acid ethyl ester. The polybasic acid may be transesterified by using one of the transesterification catalysts known in the art. Examples of such catalysts could include organic titanates, organic acids, or mineral acids.

Typically, esterification of the polybasic acid is accomplished by stirring the alcohol with a catalyst used in esterification processes such as, p-toluene sulfonic acid, sodium hydrogen sulfate, sulfuric acid, hydrochloric acid and the like, at about 15° C. to about 0° C., preferably from about 60° C. to about 70° C. An alcohol is added to the polyglycerol mixture. A solvent may be added at any time, to aid in the proper mixing of the reaction mixture. If a solvent is added, it is typically excess of the alcohol to be used.

The resulting polybasic acid ethyl ester can be filtered and extracted with any number of polar solvents. Water, ethanol, methanol, isopropanol or any combination of these is preferred. At the same time the possible side effects of ingestion of certain alcohols such as methanol must be considered. Thus, preferably ethanol is employed.

The simple alcohols employed in esterification can be any straight chain or branched, saturated or unsaturated, alcohols with from 1 to 22 carbon atoms. Preferably, the alcohol is ethanol or another alcohol that is suitable for food use. These alcohols are released into the body by the processes of intestinal digestion upon the polybasic acid ester of this invention. Since these alcohols are of low molecular weight they are absorbed into the body and contribute calories in the usual way. To keep the caloric availability as low as possible the molecular weight of the alcohol portion should therefore be as small as possible.

The polybasic acid ethyl esters employed in the preferred embodiment of this invention are ethyl esters of mixtures of dimer and trimer acid. These esters may be prepared from ethanol and polybasic acid mixtures by any of the esterification methods known in the art. This same material may also be prepared by polymerization of $C_{18}$ unsaturated fatty acids that have already been esterified with an alcohol.

The polybasic acid ethyl esters of this invention have the appearance and physical properties of normal liquid triglyceride oils. Typical values of the viscosity at 100° F. using Brookfield viscometer of the poly basic acid ethyl esters of this invention can vary from, but are not limited to, up to about 45 cPs for a high dimer mixture, up to about 150 cPs for a high trimer mixture. Since the esters of this invention have no solid component, the problem of "waxy mouthfeel" common to some other low calorie oils does not arise.

The polybasic acid ethyl esters of this invention have reduced caloric availability compared with normal triglyceride oils by virtue of the non-caloric nature of the polybasic acid portion of the ester. After ingestion, these poly basic acid ethyl esters have the property of being at least partly hydrolyzed by intestinal digestion into their component parts of simple alcohols and polybasic acids. These polybasic acids are of sufficient molecular weight that they are substantially not absorbed in the body, and are thus non-caloric. Only the alcohol portion contributes calories to the food. In the preferred embodiment of the invention the polybasic acid ethyl ester has only about 12 percent of the caloric availability of an equal weight of a normal triglyceride oil. Evidence for this at least partial digestive hydrolysis of the polymer acid ester of this invention can be obtained from in vitro testing with pancreatic lipase.

These polybasic acid ethyl esters can be employed as substitutes for oils in foods. The polybasic acid ethyl esters may be used to entirely replace the regular oil or fat or may be mixed with the regular oil to make a blend. The ratio of the blend would depend upon the desired caloric level. If an oil that is very low in calories is desired then obviously the blend would contain a greater proportion of the polybasic acid ethyl esters. The polybasic acid ethyl esters can be employed as substitutes for oils in such foods as ice cream, frozen desserts, cake, cookies, candies, snack foods, or any food product that contains a regular oil or fat.

The following examples are included solely to illustrate this propensity for hydrolysis, and are not meant to be limiting.

EXAMPLE 1

Samples of the polymer acid ester of this invention, along with triolein as control, were exposed to pancreatic lipase in a buffer solution containing bile salts. The samples of the polybasic acid ethyl esters used this test included:
  Sample 1 which was high in trimer
  Sample 2 which was high in dimer
  Control which was triolein.
The pH of the three mixtures were adjusted to a value of 7.4, and the reaction was followed for 30 minutes by autotitration with KOH to maintain a constant pH.

Results

Under these conditions Sample 1 was digested about 65 percent as much as triolein, while Sample 2 was digested about 36 percent as much as triolein. While we do not wish to be bound by theory, it is believed that the non-laxative nature of the polybasic ethyl ester is due to this at least partial digestive hydrolysis of the material. Hydrolysis of the material from the ester form to the acid form significantly increases its viscosity. As taught herein, a sample of the polybasic ethyl ester that is high in trimer acid may typically have a viscosity at 100° F. of about 150 cPs, while the free polymer acid that it would form upon hydrolysis would typically have a value of as much as 22,000 cPs. This viscosity increase alone could account for the lack of a pronounced laxative effect.

EXAMPLE 2

Preparation of Polymer Acid Ester Samples High Trimer

The starting material was a sample of polymerized $C_{18}$ fatty acids that was comprised of 2 percent monobasic acid, 18 percent dibasic acid (dimer) and 80 percent tribasic acid (trimer), with a viscosity at 100° F. of 21,500 cSt. This mixture was esterified by refluxing in excess ethanol for several hours in the presence of NaHSO$_4$, followed by concentration in vacuo to remove excess ethanol and water. The crude product was purified chromatographically on 8 equivalents of alumina eluting with a 50/50 mixture of hexanes and ethyl ether. After concentration the residual solvent was removed in vacuo (1 torr) at 80° for 4 hours. The product ester had a viscosity (at 100° F) of 140 cPs.

Intermediate Trimer

The starting material was a sample of polymer acids formed by the polymerization of $C_{18}$ fatty acids, and was comprised of 3 percent monomer acids, 35 percent dibasic acids (dimer), and 62 percent polybasic acids (trimer). The viscosity of the starting mixture was measured as 6700 cPs at 100° F. Esterification and purification were performed as above to give a product with a viscosity at 100° F. of 94 cPs.

High Dimer

The starting material was a sample of distilled polymer acids formed by the polymerization of $C_{18}$ fatty acids, and was comprised of 1 percent monomer acids, 96 percent dibasic acids (dimer), and 3 percent polybasic acids (trimer). The viscosity of the starting mixture at 100° F. was measured as 2400 cPs. Esterification and purification were performed as above to give a product with a viscosity at 100° F. of 46 cPs.

EXAMPLE 3

Animal Feeding Studies

Samples

The Intermediate Trimer and High Dimer polymer acid esters were prepared according to the examples above. Male and female rats were fed a laboratory chow diet containing 5 percent by weight over a two week period of Intermediate Trimer or High Dimer. Feces were collected and analyzed for lipid content by the Jover fecal analysis method, see A. Jover and R. S. Gordon, "Procedure for Quantitative Analysis of Feces With Special Reference to Fecal Fatty Acids", 59 Journal of Laboratory Clinical Medicine at 878. By using this method the percentage of carboxylic acid sites present in the feed was determined that were recovered in the feces. By the Jover method 82 percent of the polymer acid of the High Dimer sample was recovered in the feces, while 98 percent of the polymer acid of Intermediate Trimer sample was recovered. The rats that were fed the chow containing the Intermediate Trimer did not exhibit any anal leakage, nor did the rats that were fed the chow that contained the High Dimer.

Control

Male and female rats were also fed a Control: laboratory chow which contained 5 percent heavy mineral oil for two weeks. These rats developed anal leakage within 4 days of their initial feeding and the leakage persisted for the balance of the two week period.

What is claimed is:

1. A method of reducing calories in a food composition having an edible oil component, where the method comprises replacing an effective portion of the edible oil with an polybasic acid ethyl ester wherein the polybasic acid ethyl ester is made by esterifying a polybasic acid that is a polymerization of two to three unsaturated $C_{18}$ fatty acids.

2. The method of reducing calories in a food composition having an edible oil component as in claim 1 where the polybasic acid comprises a mixture of unreacted monomeric fatty acid, dimer acid, trimer acid or mixtures of acids.

3. The method of reducing calories in a food composition having an edible oil component as in claim 2 where the mixture of unreacted fatty acids contains trimer and dimer acid.

4. The method of reducing calories in a food composition having an edible oil component as in claim 3 where the unreacted mixture contains less than 5 weight percent monomeric fatty acid.

5. The method of reducing calories in a food composition having an edible oil component as in claim 4 where the unreacted mixture contains less than 1 weight percent monomeric fatty acid.

6. The method of reducing calories in a food composition having an edible oil component as in claim 1 where the polybasic acid is polymerized by about 1 to about 80 weight percent trimer acid and about 20 to about 99 weight percent dimer acid.

7. The method of reducing calories in a food composition having an edible oil component as in claim 6 where the polybasic acid is polymerized by about 1 to about 60 weight percent trimer acid and about 99 to about 40 weight percent dimer acid.

8. The method of reducing calories in a food composition having an edible oil component as in claim 7 where the polybasic acid is polymerized by about 60 weight percent trimer acid and about 40 weight percent dimer acid.

9. The method of reducing calories in a food composition having an edible oil component as in claim 1 where the polybasic acid is esterified with an alcohol having 1 to 22 carbon atoms.

10. The method of reducing calories in a food composition having an edible oil component as in claim 9 where the alcohol is ethanol.

* * * * *